United States Patent
Yamazaki et al.

(10) Patent No.: US 6,555,137 B1
(45) Date of Patent: Apr. 29, 2003

(54) SUCRALFATE-CONTAINING COMPOSITION AND PROCESS FOR THE PREPARATION THEREOF

(75) Inventors: Tamotsu Yamazaki, Tokyo (JP); Heiji Ikushima, Toyama (JP); Tetsuo Shirai, Toyama (JP)

(73) Assignees: Chugai Seiyaku Kabushiki Kaisha, Tokyo (JP); Fuji Chemical Industry Co., Ltd., Kamiichi (JP)

(*) Notice: Subject to any disclaimer, the term of this patent is extended or adjusted under 35 U.S.C. 154(b) by 0 days.

(21) Appl. No.: 09/446,871

(22) PCT Filed: Jun. 15, 1998

(86) PCT No.: PCT/JP98/02615
§ 371 (c)(1),
(2), (4) Date: Dec. 29, 1999

(87) PCT Pub. No.: WO99/00112
PCT Pub. Date: Jan. 7, 1999

(30) Foreign Application Priority Data

Jun. 30, 1997 (JP) ................................. 9-173991

(51) Int. Cl.[7] .......................... A61K 9/10; A61K 9/16; A61K 9/26; A61K 9/58; A61P 1/04

(52) U.S. Cl. ..................... 424/484; 424/497; 424/462; 424/469; 424/470; 424/514; 424/927

(58) Field of Search ............................... 424/405, 462, 424/469–70, 497, 484

(56) References Cited

U.S. PATENT DOCUMENTS 4,433,076 A * 2/1984 Bauer et al.

FOREIGN PATENT DOCUMENTS

EP 0867191 * 5/1997

* cited by examiner

Primary Examiner—Edward J. Webman

(57) ABSTRACT

A coated antacid comprising sucralfate and an antacid inhibits decline in the adhesion characteristics of sucralfate whereby the drug ingested can reliably show its effect in the stomach. This coated antacid not only shows the mucosa repairing effect of sucralfate itself, but also shows the antacid effect and the gastric mucosa protective effect of the coated antacid, thereby synergistically producing an excellent antiulcer effect and an excellent ulcer inhibiting/healing effect.

20 Claims, 1 Drawing Sheet

SUCRALFATE-CONTAINING COMPOSITION AND PROCESS FOR THE PREPARATION THEREOF

CROSS REFERENCE TO RELATED APPLICATION

The present application is the national stage under 35 U.S.C. 371 of PCT/JP98/02615, filed Jun. 15, 1998.

TECHNICAL FIELD

This invention relates to a composition comprising sucralfate and a coated antacid with controlled onset of reaction (hereinafter referred to as a coated antacid). The composition of the present invention is useful per se as a pharmaceutical composition, especially a gastrointestinal drug, and also as a pharmaceutical base composition for production of other medicines by its blending with appropriate active ingredients.

When the composition of the present invention is taken orally as a drug, sucralfate, a constituent of the composition, reacts with gastric acid in the stomach to form an adhesive substance (paste), which adheres to the mucosa, exhibiting an antiulcer effect and an ulcer inhibiting/healing effect. Then, the coated antacid held in the paste shows a persistent antacid action. That is, the present invention relates to a DDS-type composition as a gastrointestinal drug comprising sucralfate and an antacid, which permits the pharmacological effect of sucralfate to appear fully, and the antacid to dwell in the stomach, thereby revealing its antacid effect for a long time. The invention is also concerned with a method for producing the composition.

BACKGROUND ART

Sucralfate is a basic aluminum sucrose sulfate. As a peptic ulcer treating agent having a stromal protein protecting effect (gastric mucosa protecting effect), a gastric juice pepsin activity inhibiting effect, and an antacid effect, sucralfate is widely used for alleviation of gastric ulcer, duodenal ulcer, or gastric mucosal lesions in diseases, such as erosion, bleeding, redness or edema; for treatment of acute gastritis; and at the acute aggravated stage of chronic gastritis. Sucralfate shows a therapeutic effect by forming a bioadhesive paste upon reaction with gastric acid in the digestive tract to generate a local protective barrier, which protects the mucous membrane of the digestive tract from an excess of gastric acid, and promotes the in vivo repairing action on the mucosa.

Sucralfate has so far been supplied as a single-component pharmaceutical preparation, but in the clinical setting, it is generally used as a formulation combined with an antacid, etc. As an over-the-counter drug, sucralfate has been used as combined drugs. in the form of tablets, granules, fine granules, or suspension, in combination with various antacids, gastrointestinal drugs, or analgesic antispasmodics. To bind sucralfate to the site of ulceration effectively, it is important that a sucralfate preparation be rapidly disintegrated, and dispersed. For example, proposal has been made for a suspension comprising natural gums, deflocculants, and sucralfate (Japanese Unexamined Patent Publication No. 5-238938), or a sucralfate preparation obtained by adding a plasticizer to sucralfate, and granulating the mixture in molten condition (Japanese Unexamined Patent Publication No. 8-104637).

However, sucralfate is insoluble in water, and combined gastrointestinal drugs comprising sucralfate and various antacids lead to the instantaneous neutralization of gastric acid with the antacids to increase the pH in the stomach. Thus, the adhesion of sucralfate which should be generated upon reaction with gastric acid is delayed or inadequate, thereby failing to show a sufficient gastric mucosa protecting effect. Consequently, its antiulcer effect and its ulcer inhibiting/healing effect have sometimes been diminished.

DISCLOSURE OF THE INVENTION

The present invention aims to develop a coated antacid prescribed as a combined drug containing sucralfate. The combined drug, upon ingestion, prevents the deterioration of the adhesive substance forming characteristics of sucralfate, and can reliably exhibit its actions in the stomach.

That is, the combined drug suppresses the reaction of the antacid with gastric acid at the initial stage after it arrives at the stomach. By so doing, the drug enhances the solubility of sucralfate in the stomach, and permits sucralfate to show its antiulcer effect and its ulcer inhibiting/healing effect. Furthermore, the drug can make the antacid effect of the antacid persist sufficiently and for a long time after the sucralfate amply adheres to the mucosa. If the drug also contains other pharmacologically active ingredients, release of these active ingredients can also last for a long period of time. The present invention aims at developing a gastrointestinal drug which fulfills these requirements, and an antacid to be incorporated into this combined prescription.

The inventors conducted extensive studies to resolve this challenge. As a result, they found that a coated antacid obtained, for example, by spray drying a slurry of an antacid, together with a coating agent and a specific plasticizer, suspended in a suitable medium can control the onset of the reaction between gastric acid and the antacid. This coated antacid is an antacid having DDS function which can strictly control the onset of the reaction between gastric acid and the antacid, because the amount of mixing of the plasticizer to be spray dried, such as a polyethylene glycol, is adjusted to control the porosity and the pore size for the pore formation of the spray dried particles. Conventional sustained release antacids are slowly released. By contrast, the coated antacid of the present invention is characterized by delaying the onset of the reaction of the antacid.

The inventors found that a composition comprising the coated antacid and sucralfate, when orally administered as a gastrointestinal drug, not only shows the mucosa repairing action of sucralfate fully, but acts synergistically with the antacid effect and gastric mucosa protecting effect of the incorporated coated antacid, thus exhibiting an excellent antiulcer action and an excellent ulcer inhibiting and healing action. Based on this finding, they accomplished the present invention. When other pharmacologically active ingredient is incorporated in the composition of the invention, this active substance can be sustainedly released for a long time.

BEST MODE FOR CARRYING OUT THE INVENTION

Figure 1:
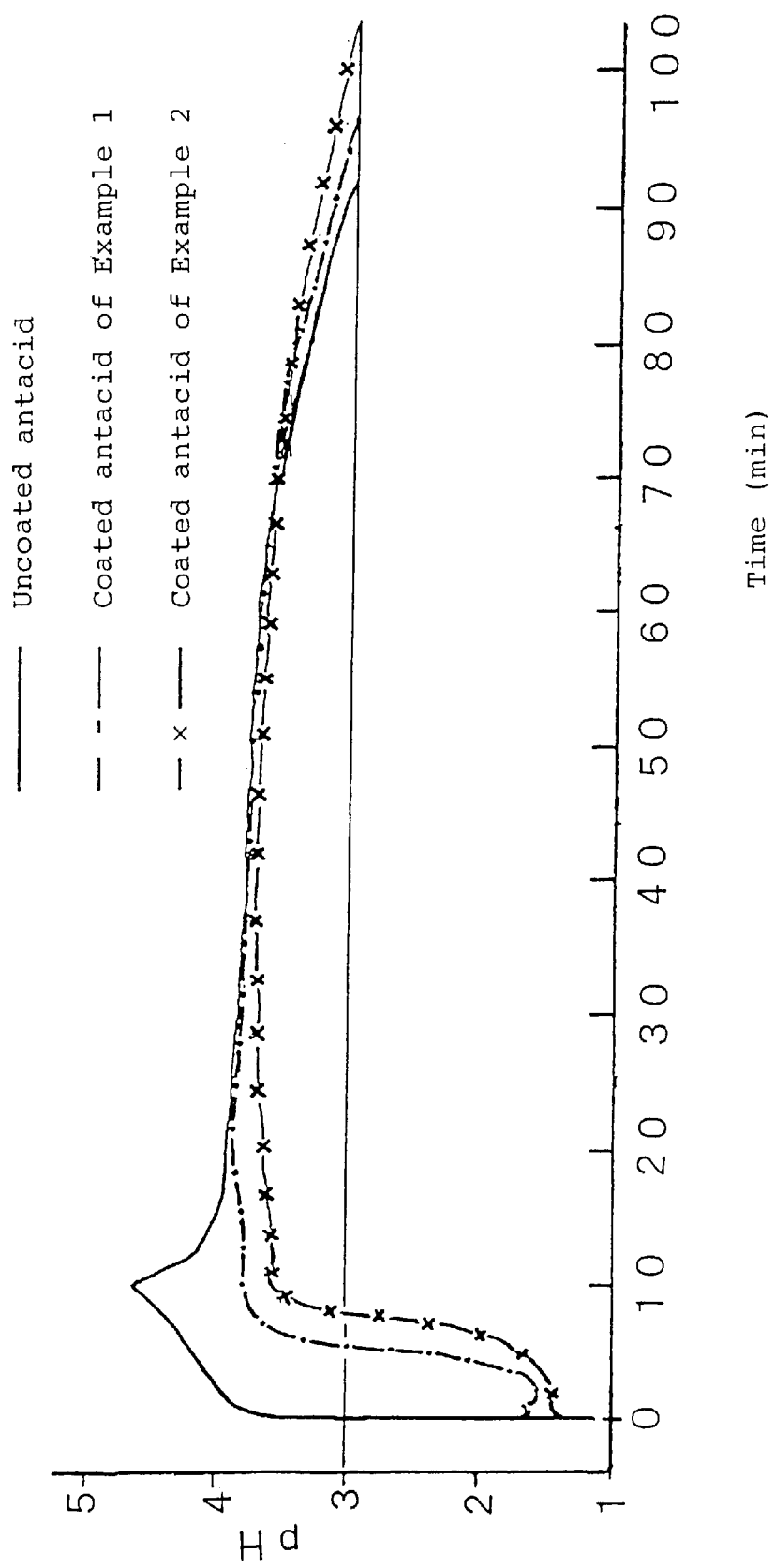
FIG. 1 is a view showing the results of an acid consuming capacity test of coated antacids of Examples 1 and 2 and an uncoated antacid in an artificial gastric juice model by the modified Fuchs method.

The present invention relates to a composition comprising sucralfate and a coated antacid and suitable for use as a gastrointestinal drug. The invention is also concerned with a coated antacid obtained by spray drying a suspension of a plasticizer, a coating agent, and an antacid. The time when the reaction is initiated, or "the onset of reaction", a wording used in the present invention, refers to a period of time from the start of the modified Fuchs test until pH rapidly begins to increase, as will be described later on in a Comparative Example.

When the composition of the present invention is used as a gastrointestinal drug, the coated antacid contained in the preparation shows no antacid action at the initial stage of oral administration. During this period, sucralfate dissolved in gastric acid preferentially adheres to the stomach wall to form an adhesive membrane, in which the antacid and other active ingredients are held. Then, the antacid component in the coated antacid reacts with gastric acid to maintain the pH in the stomach within an optimal range for a long time. By this mechanism, sucralfate, the antacid and other active ingredients show an antiulcer action and an ulcer inhibiting/healing action in a complex manner.

In detail, the present invention claims a gastrointestinal drug comprising sucralfate and a coated antacid designed such that the onset of reaction of sucralfate in the stomach and the onset of reaction of the antacid in the stomach will be controlled; the time taken until the optimal pH is reached in the stomach will be in a specific range; and the duration of persistence of the optimal pH will be prolonged.

The onset of reaction for the coated antacid in the present invention is 30 seconds or more, preferably 1 minute or more, and more preferably 5 minutes or more, after a sample is introduced, in accordance with the modified Fuchs method to be described later on. The time to pH 3.5 according to this method is 1 minute or more, preferably 2 minutes or more, and more preferably 5 minutes or more.

The composition of the present invention, as a gastrointestinal drug, can be prepared by blending sucralfate and the coated antacid in a suitable manner. Preferred dosage forms are a preparation for oral administration which comprises sucralfate and the coated antacid as a mixture in the same preparation, and a preparation for oral administration which contains sucralfate and the coated antacid separately in the same preparation.

Sucralfate for use in the present invention can be used as such in the composition, but may be used in the form of fine granules or a powdered drug after addition of appropriate additives, if desired.

For use as a gastrointestinal drug, the composition of the present invention-can be made into a form, such as powder, fine granules, granules, tablets, capsules, or chewable tablets, by suitably blending sucralfate and the coated antacid, and further incorporating other gastrointestinal active ingredients according to a purpose to be attained.

Methods for producing the composition of the present invention and a gastrointestinal drug comprising this composition will be described more concretely.

Sucralfate for use in the invention is not restricted, and any sucralfate generally used poses no problem. Examples are dry sucralfate powder obtained by, say, spray drying undried sucralfate powder which has been obtained by reacting basic aluminum chloride with sucrose polysulfuric ester, in accordance with the method described in Japanese Patent Publication No. 44-11673 or Japanese Patent Publication No. 44-16037; sucralfate designated by the Japanese Pharmacopoeia; fine sucralfate powder formed by further pulverizing dry sucralfate powder, which has been obtained by a conventional method, in accordance with the method described in Japanese Unexamined Patent Publication No. 8-104637; and a preparation prepared by adding a plasticizer to the fine powder, mixing them, and then granulating the mixture in molten (or adherent) condition under heat.

The coated antacid used in the present invention is characterized in that its film is not a complete film, because the solvent scatters during spray drying to form pores in the particles. When a water-insoluble coating agent, for example, is used as a coating agent, the resulting film, if being a complete film, results in delayed release of the antacid, failing to exhibit an antacid action fully. The particles obtained by the manufacturing method of the present invention, if they use an insoluble coating agent, in particular, can show a desired antacid effect, because of the presence of the pores. By setting the manufacturing conditions, this coated antacid can be made to control the porosity and average pore diameter in pore formation of spray dried particles, and strictly control the onset of reaction with gastric acid. Thus, the coated antacid of the present invention has DDS function, and enables the onset of reaction between the antacid and gastric juice to be adjusted as desired.

The coated antacid can be produced by spray drying a suspension of a plasticizer, a coating agent, and an antacid. More concretely, the coated antacid can be produced by dissolving a plasticizer and a coating agent in a suitable medium, such as water or a mixture of water and ammonia, in which the plasticizer and the coating agent can dissolve, dispersing an antacid in the solution to obtain a suspension, and spray drying the suspension.

In preparing the coated antacid, it is possible, if desired, to add additives, such as lactose, mannitol, and sucrose, further, thereby helping control the onset of reaction. Furthermore, gastrointestinally active ingredients, such as crude drugs, may be added, and the mixture may be spray dried.

Examples of the antacid are those showing a gastric mucosa, protecting effect as well as an antacid effect, such as magnesium aluminometasilicate, magnesium aluminosilicate, synthetic hydrotalcite, synthetic aluminum silicate, magnesia alumina hydrate, aluminum hydroxide-sodium bicarbonate coprecipitate, aluminum hydroxide-magnesium carbonate-calcium carbonate coprecipitate, dried aluminum hydroxide gel, magnesium hydroxide, and precipitated calcium carbonate. Preferred examples are magnesium aluminometa-silicate and magnesium aluminosilicate which are amorphous and porous.

In the present invention, two or more of these substances may be used in combination.

The amount of the antacid used differs according to the type, amount, etc. of the antacid, plasticizer, or coating agent used, and has no restrictions. Preferably, its amount is 50 to 90% by weight, more preferably 50 to 75% by weight, based on the weight of the coated antacid.

As the coating agent, cellulose derivatives and synthetic polymeric compounds which are generally used are exemplified. However, the single use of polymeric compound, which easily dissolves with gastric juice, is not appropriate. Preferably, a water soluble coating agent, or a non-water-soluble coating agent, such as an enteric coating agent, is exemplified.

Examples of the water soluble coating agent are cellulose derivatives, such as hydroxypropyl methylcellulose (HPMC), hydroxypropyl cellulose (HPC), methylcellulose (MC), hydroxyethyl cellulose (HEC), and hydroxymethyl cellulose (HMC).

Examples of the enteric coating agent are cellulose derivatives such as hydroxymethyl cellulose phthalate (HPMCP), and hydroxypropyl methylcellulose acetate succinate (HPMCAs); and synthetic polymeric compounds such as methacrylate copolymer, methacrylate-ethyl acrylate copolymer, and methacrylate-methyl methacrylate copolymer.

Examples of the non-water-soluble coating agent are carboxymethylethylcellulose (CMEC), cellulose acetate phthalate (CAP), ethyl acrylate-methyl methacrylate-ethyl acrylate copolymer, and ethylcellulose (EC).

In the present invention, one or more of the coating agents enumerated above may be selected as desired, and used. HPMC, HPC, HMC and MC are preferred.

The amount of the coating agent used differs according to the type, amount, etc. of the antacid and water-soluble low-melting waxes used, and is not restricted. In the case of HPMC, for example, its amount is preferably 10 to 50% by weight, and more preferably 25 to 50% by weight, based on the total weight of the coating agent.

As the plasticizer usable in the present invention, polyethylene glycol, polyoxyethylene polyoxypropylene glycol, and their mixtures are exemplified. Preferred examples are polyethylene glycols having a melting point of 40 to 70° C., such as polyethylene glycol 4000 (melting point 53–57° C.), polyethylene glycol 6000 (melting point 56–61° C.), and polyethylene glycol 20000 (melting point 56–64° C.). Polyethylene glycol 6000 is particularly preferred.

The amount of the plasticizer used differs according to the type, combination, amount, etc. of the antacid, and the coating agent used, and is not restricted. In the case of PEG 6000, for example, its amount is preferably 0.1 to 15% by weight, and more preferably 2.5 to 10% by weight, based on the weight of the coating agent used in the coated antacid.

The method for producing the coated antacid is preferably the aforementioned spray coating. For further processing, granulation can be performed by ordinary spray drying, fluidized bed granulation, or agitating granulation.

The viscosity of the slurry used for spray drying differs according to the types of the antacid and the plasticizer, and is not restricted. Normally, it is 1000 cp or less, and for HPMC, for example, about 50 to 500 cp is desirable.

The coated antacid can be processed into fine particles, fine granules, compound powder, granules, pills, capsules, and tablets, in addition to a powdered drug obtained by the spray drying. Where necessary, the coated antacid can be used in different forms by the use of suitable additives for the desired form, such as preservatives, buffers, flavors, bulking agents, binders, lubricants, disintegrants, colorants, sweetening agents, adsorbents, viscosity-increasing agents, and suspending agents, in addition to plasticizers such as the aforementioned polyethylene glycols. If desired, the onset of reaction, and the duration of reaction can be changed by changing the particle size.

The amount of the coated antacid incorporated is not restricted, but preferably is an appropriate amount which will not inhibit the adhesion of sucralfate. The coated antacid used in the present invention has undergone scattering of the solvent during spray drying, and has pores formed in its particles. Thus, its film is not a complete film. As a result, at an initial stage after administration, the coated antacid delays reaction with gastric acid, causing a lag time. However, if a complete film is formed, an appropriate lag time can be generated, by suitably selecting the composition of the film (e.g., a combination such as that of a non-water-soluble coating agent and a water-soluble additive).

The amount of sucralfate incorporated in the composition of the present invention as a gastrointestinal drug is not restricted. Preferably, a single dose of 300 to 1,200 mg which is the usual dose of sucralfate, more preferably 500 to 1,080 mg, is contained in a unit preparation.

The amount of the coated antacid incorporated is not restricted, either. However, it is desirable that such an amount as can be expected to show efficacy as an antacid be incorporated (such an amount is selected according to the type of the antacid). If the antacid is magnesium aluminosilicate or synthetic hydrotalcite, for example, 500 mg to 1.4 g is a generally used single dose.

The composition of the present invention, as a gastrointestinal drug, is characterized by containing sucralfate and the coated antacid as main ingredients. Sucralfate and the coated antacid may be incorporated in a mixed state into the same preparation, or may be incorporated in a separate state into the same preparation. The gastrointestinal drug of the present invention may contain not only these main ingredients, but also other ingredients for so-called "general-purpose drugs for the stomach and bowels," such as stomachics, digestives, cholagogues, and gastric mucosa protectives, and further substances such as acetylcholine inhibitors and local anesthetics.

H2 receptor antagonists, such as cimetidine, ranitidine, famotidine, nizatidine, and roxatidine acetate, may also be incorporated.

To form the composition of the invention into a preparation, suitable materials, such as vehicles and perfumes, may be added, mixed by means of, say, a V blender, and used in an arbitrary oral dosage form, such as fine granules, powder, granules, pills, capsules, tablets, chewables, or troches.

Sucralfate, the coated antacid, a vehicle, etc. may be granulated in a mixed state by means of a fluidized bed granulator or an agitating granulator, if desired, with the additiodn of sugars or perfumes to form the composition of the invention. Alternatively, the composition may be one coated with a rapidly water-soluble coating agent such as purified sucrose.

As a gastrointestinal drug, the composition of the present invention may further contain the following substances, in addition to the above-mentioned additives: Stomachic galenicals, such as aloe, cinnamon, magnoliae cortex, ginger, atractylodis lanceae rhizoma, and ginseng; cholagogues, such as ursodesoxycholic acid, dehydrocholic acid, and bile acid; galenicals for controlling intestinal function, such as geranii herba; analgesic, antispasmodic galenicals, such as corydalis tuber, and glycyrrhiza; and mucosa repairing galenicals, such as mallotus bark.

The composition of the present invention may also contain mucosa repairing agents, such as sodium azulene sulfonate, aldioxa, glycyrrhizic acid and its salts, glycyrrhiza extract, L-glutamic acid, copper chlorophyllin potassium, histidine hydrochloride, swine gastric wall pepsin degradation product, and methylmethionine sulfonium chloride.

The present invention will be described in greater detail by reference to the Examples.

EXAMPLE 1

Method for Producing Coated Antacid

3 Grams of polyethylene glycol 6000 was dissolved in 440 g of water with stirring by means of a homomixer. 25 Grams of hydroxypropyl methylcellulose (TC-5R, a registered trademark, Shin-Etsu Chemical) was dissolved in the solution with stirring. Then, 50 g of magnesium aluminosilicate (Neusilin A, a registered trademark, Fuji Chemical Industry) was dispersed with stirring. The resulting slurry was spray dried with a spray dryer (Mobileminor, Nilo) to obtain 75 g of spray dried particles.

The spray drying conditions were an inlet temperature of about 230° C., an outlet temperature of 75° C., a flow rate of 1,500 (ml/hr), and a disc revolution speed of 25,000 (rpm).

The resulting particles had a drying loss of 6.9% (105° C., 3 hr), a specific volume of 6.5 (ml/g), and an antacid power of 155.1 (ml/g).

The onset of reaction (lag time) according to the modified Fuchs test was 200 seconds, the time to pH 3.5 was 390 seconds, and the duration of pH 3.0 was 97.5 minutes.

EXAMPLES 2 TO 7

In the method for production in Example 1, the types of the plasticizer, the coating agent, and the antacid, and their amounts used were changed as shown in Table 1 to prepare coated antacids of Examples 2 to 7. The onset of reaction (lag time), the time to pH 3.5, and the duration of pH 3.0 of the respective coated antacids were as shown in Table 1.

Comparative Example 1

50 g of magnesium aluminosilicate was dispersed in 440 g of water with stirring. The resulting slurry was spray dried in the same manner as in Example 1 to obtain 45 g of spray dried particles.

The onset of reaction of the resulting spray dried antacid was within 5 seconds, the time to pH 3.5 was 12 seconds, and the duration of pH 3.0 was 85 minutes.

For the coated antacids of the present invention and the uncoated antacid, the time courses of pH determined by the modified Fuchs test are shown in FIG. 1.

chamber (37±2° C.), and stir with a stirrer (300 revolutions/min).

(2) Charge 1 g of a sample, and immediately actuate an automatic recorder connected to a pH meter, and a stopwatch.

(3) Record the onset of reaction that is the period of time until the pH begins to rise rapidly after start of the test, and also record the time until pH 3.5 is reached.

(4) Exactly 10 minutes after actuation, pour 2 ml/min of a 0.1 N-hydrochloric acid solution into the beaker by means of a micropump.

(5) Record the period of time during which pH 3.0 persists.

Test Example
Usefulness of the Invention in Biological Test

The usefulness of the gastrointestinal drug of the present invention investigated in a biological test will be described. The biological test was performed by the method of Robert et al. which evaluates a test substance by the effect of inhibiting an ethanol-induced injury to the gastric mucosa. Details of this method will be offered below.

① Preparation of Sucralfate

A wet powder of sucralfate was suspended in water, and homogenized. The resulting slurry was spray dried with a spray dryer S-250N/R to obtain a spray dried powder.

② Formulation of a Gastrointestinal Drug

The above spray dried sucralfate powder and the coated antacid obtained in each of the Examples were mixed by the customary method at a ratio corresponding to 1 part by weight of the coated antacid, as an antacid, to 1 part by weight of sucralfate.

<Rat Gastric Injury Inhibition Test>

Next, a test for rat gastric mucosa injury inhibition by the gastrointestinal drug of the present invention is described.

TABLE 1

| | Amount of each material charged | | | | Antacid activity of coated antacid | | |
|---|---|---|---|---|---|---|---|
| Ex. No. | Antacid (g) | Coating agent (g) | Plasticizer (g) | Solvent (g) | Onset of reaction (sec) | Time to pH 3.5 (sec) | Duration of pH 3.0 (min) |
| 2 | Magnesium aluminosilicate (50) | HPMC (50) | PEG6000 (5) | Water (720) | 300 | 525 | 104 |
| 3 | Magnesium aluminometasilicate (50) | HPMCP (25) | PEG6000 (3) | Water-aqueous ammonia (340-14) | 120 | 129 | 96 |
| 4 | Magnesium aluminosilicate (50) | HPMCP (50) | PEG6000 (5) | Water-aqueous ammonia (670-28) | 150 | 180 | 60 |
| 5 | Magnesium aluminometasilicate (50) | EC (25) | Triethyl citrate (5) | Water-ethanol (216-504) | 60 | 84 | 92 |
| 6 | Dried aluminum hydroxide gel (50) | HPMC (25) | PEG6000 (3) | Water (440) | 130 | 148 | 80 |
| 7 | Synthetic hydrotalcite (50) | HPMC (25) | PEG6000 (3) | Water (430) | 150 | 190 | 115.5 |

<Modified Fuchs Test>

The modified Fuchs test was conducted by the following procedure using a device comprising a micropump, a 0.1 N-hydrochloric acid solution reservoir, a magnetic stirrer with a tachometer, a thermostatic chamber with a thermostat, a pH meter, and an automatic recorder:

(1) Immerse a beaker containing 50 ml of a 0.1 N-hydrochloric acid solution (f=1.00) in a thermostatic Effect of Combined Use of Gastrointestinal Drug and Antacid in a Rat Ethanol-induced Injury Model The effect of sucralfate and various antacids in inhibiting ethanol-induced rat stomach injury was investigated.

Experimental Materials and Methods

Animals:

Groups of five 6-week-old SD male rats (Nippon SLC) were used.

Test drugs:

Sucralfate (Chugai Pharmaceutical), sodium bicarbonate (Junsei Kagaku), synthetic hydrotalcite (Kyowa Chemical Industry), magnesium aluminometasilicate (Neusilin, a registered trademark, Fuji Chemical Industry), coated antacids (Example 1, Example 2).

Preparation of test drug suspension and control:

The test drug was suspended in 2% gum arabic, and 2 ml/kg off the suspension was orally administered. As a control, a 2% aqueous solution of gum arabic was prepared, and 2 ml/kg of the solution was orally administered.

Experimental method:

A rat, which had been given no food and no water for 24 hours, was administered a predetermined dose of sucralfate. A predetermined dose of the antacid was administered immediately (simultaneously). One hour later, 1 ml of ethanol was orally administered. One hour later, the stomach was removed, and the length of an injury occurring in the gastric gland mucosa (injury index) was measured.

The dose of sucralfate was set at 50 mg/kg, which was determined by preliminary experiments to be such an amount that the injury inhibition rate (percentage inhibition of injury by the test drug relative to the control) would be about 80%.

The dose of the antacid preparation was set at two levels, i.e., 50 mg/kg and 200 mg/kg, for comparative study, in consideration of the dose of sucralfate.

<Test Results>

The results are shown in Table 2.

TABLE 2

| Experiment No. | Test drug (dose: mg/kg) | Injury inhibition rate (%) |
|---|---|---|
| 1 | Sucralfate 50 (alone) | 76.5 |
|   | Sucralfate 50 + Sodium bicarbonate 50 | 39.7 |
|   | Sucralfate 50 + Sodium bicarbonate 200 | 35.4 |
| 2 | Sucralfate 50 (alone) | 79.2 |
|   | Sucralfate 50 + Synthetic hydrotalcite 50 | 70.9 |
|   | Sucralfate 50 + Synthetic hydrotalcite 200 | 23.5 |
| 3 | Sucralfate 50 (alone) | 78.0 |
|   | Sucralfate 50 + Neusilin 50 | 52.5 |
|   | Sucralfate 50 + Neusilin 200 | 25.2 |
|   | Sucralfate 50 (alone) | 81.0 |
| 4 | Sucralfate 50 + Coated antacid of Ex. 1 50 | 86.5 |
|   | Sucralfate 50 + Coated antacid of Ex. 1 200 | 87.6 |
|   | Sucralfate 50 + Coated antacid of Ex. 2 50 | 89.1 |
|   | Sucralfate 50 + Coated antacid of Ex. 2 200 | 84.3 |

Experiment Nos. 1 to 3 show comparisons between treatment with sucralfate alone and combined treatment with sucralfate and the unprocessed antacid. All the results indicate that the combined treatment decreased the gastric mucosa injury inhibition rate than did the single treatment, with sucralfate. As shown in Experiment No. 4, on the other hand, the combined treatment with sucralfate and the coated antacid of the present invention gave the injury inhibition rate higher than did the sucralfate single treatment. These findings demonstrate the usefulness of the coated antacid.

Formulation Example 1

Tablets (Four Tablets)

In accordance with the customary manufacturing method for tablets, a preparation having the following recipe was prepared:

| | |
|---|---|
| Sucralfate | 500 mg |
| Coated antacid of Example 1 | 640 mg |
| Sodium azulene sulfonate | 2 mg |
| L-glutamine | 130 mg |
| Mannitol | 187 mg |
| Corn starch | 140 mg |
| Magnesium stearate | 1 mg |

Formulation Example 2

Fine Granules

Fine granules were prepared by the customary method using the following recipe:

| | |
|---|---|
| Spray dried sucralfate powder | 500 mg |
| Coated antacid of Example 1 | 640 mg |
| Purified sucrose | 160 mg |
| Perfume | Trace amount |

Formulation Example 3

Capsules (Five Capsules)

Capsules were prepared by the customary method using the following recipe:

| | |
|---|---|
| Spray dried sucralfate powder | 500 mg |
| Coated antacid of Example 1 | 640 mg |
| Purified sucrose | 160 mg |
| Perfume | Trace amount |

Industrial Applicability

The present invention successfully provided a gastrointestinal drug which enables sucralfate to adhere fully at an initial stage after reaching into the stomach, and which enables the coated antacid to maintain an optimal pH value, as determined by the modified Fuchs test, for a long time after adhesion of sucralfate, thereby enhancing an antiulcer effect and an ulcer inhibiting/healing effect synergistically. The invention was also able to provide a method for producing the gastrointestinal drug.

What is claimed is:

1. A pharmaceutical composition for delayed release of an antacid in the stomach, in unit dosage form comprising (A)

300–1200 mg of sucralfate, and (B) 500–1400 mg of a coated antacid,
wherein the coating of said coated antacid is a cellulose derivative or a synthetic polymeric compound which is not easily dissolvable in the presence of gastric juice.

2. A pharmaceutical composition according to claim 1 wherein said composition further comprises a drug selected from the group consisting of stomachics, digestives, cholagogues, gastric mucosa protectives, acetylcholine inhibitors, and local anesthetics.

3. A pharmaceutical composition according to claim 1 wherein the sucralfate and the coated antacid are contained in a mixed state in the same unit dosage form.

4. A pharmaceutical composition according to claim 1, wherein the sucralfate and the coated antacid are contained in separate states in the same unit dosage form.

5. A pharmaceutical composition according to claim 1 wherein said coated antacid contains an antacid, a plasticizer, and a coating agent.

6. A pharmaceutical composition according to claim 2 wherein said coated antacid contains an antacid, a plasticizer, and a coating agent.

7. A pharmaceutical composition according to claim 3 wherein said coated antacid contains an antacid, a plasticizer, and a coating agent.

8. A pharmaceutical composition according to claim 4 wherein said coated antacid contains an antacid, a plasticizer, and a coating agent.

9. A pharmaceutical composition according to claim 1 wherein the antacid of said coated antacid is selected from the group consisting of magnesium aluminometasilicate, magnesium aluminosilicate, synthetic hydrotalcite, synthetic aluminum silicate, magnesia alumina hydrate, aluminum hydroxide-sodium bicarbonate coprecipitate, aluminum hydroxide-magnesium carbonate-calcium carbonate coprecipitate, dried aluminum hydroxide gel, precipitated calcium carbonate, and mixtures thereof.

10. A pharmaceutical composition according to claim 2 wherein the antacid of said coated antacid is selected from the group consisting of magnesium aluminometasilicate, magnesium aluminosilicate, synthetic hydrotalcite, synthetic aluminum silicate, magnesia alumina hydrate, aluminum hydroxide-sodium bicarbonate coprecipitate, aluminum hydroxide-magnesium carbonate-calcium carbonate coprecipitate, dried aluminum hydroxide gel, precipitated calcium carbonate, and mixtures thereof.

11. A pharmaceutical composition according to claim 3 wherein the antacid of said coated antacid is selected from the group consisting of magnesium aluminometasilicate, magnesium aluminosilicate, synthetic hydrotalcite, synthetic aluminum silicate, magnesia alumina hydrate, aluminum hydroxide-sodium bicarbonate coprecipitate, aluminum hydroxide-magnesium carbonate-calcium carbonate coprecipitate, dried aluminum hydroxide gel, precipitated calcium carbonate, and mixtures thereof.

12. A kit comprising a pharmaceutical composition and indicia designating said composition as a gastrointestinal drug, said pharmaceutical composition comprising the pharmaceutical composition of claim 1.

13. A pharmaceutical composition for delayed release of an antacid in the stomach, consisting essentially of
(A) 300–1200 mg of sucralfate,
(B) 500–1400 mg of a coated antacid, and
(C) a drug selected from the group consisting of stomachics, digestives, cholagogues, gastric mucosa protectives, acetylcholine inhibitors, and local anesthetics,
wherein the coating of said coated antacid is a cellulose derivative or a synthetic polymeric compound which is not easily dissolvable in the presence of gastric juice.

14. A pharmaceutical composition for delayed release of an antacid in the stomach, consisting essentially of
(A) 300–1200 mg of sucralfate, and
(B) 500–1400 mg of a coated antacid,
wherein the antacid of said coated antacid is an antacid selected from the group consisting of magnesium aluminometalsilicate, magnesium aluminosilicate, synthetic hydrotalcite, synthetic aluminum silicate, magnesia alumina hydrate, aluminum hydroxide-sodium bicarbonate coprecipitate, aluminum hydroxide-magnesium carbonate-calcium carbonate coprecipitate, dried aluminum hydroxide gel and precipitated calcium carbonate,
wherein the coating of said coated antacid is a cellulose derivative or a synthetic polymeric compound which is not easily dissolvable in the presence of gastric juice.

15. A pharmaceutical composition for delayed release of an antacid in the stomach, consisting essentially of
(A) 300–1200 mg of sucralfate,
(B) 500–1400 mg of a coated antacid, and
(C) a drug selected from the group consisting of stomachics, digestives, cholagogues, gastric mucosa protectives, acetylcholine inhibitors and local anesthetics, wherein the antacid of said coated antacid is an antacid selected from the group consisting of magnesium aluminometasilicate, magnesium aluminosilicate, synthetic hydrotalcite, synthetic aluminum silicate, magnesia alumina hydrate, aluminum hydroxide-sodium bicarbonate coprecipitate aluminum hydroxide-magnesium carbonate-calcium carbonate coprecipitate, dried aluminum hydroxide gel and precipitated calcium carbonate,
wherein the coating of said coated antacid is a cellulose derivative or a synthetic polymeric compound which is not easily dissolvable in the presence of gastric juice.

16. A pharmaceutical composition according to claim 1 wherein the coating of said coated antacid is porous.

17. The pharmaceutical composition of claim 1, wherein said coating is selected from the group consisting of hydroxypropyl methylcellulose, hydroxypropyl cellulose, methylcellulose, hydroxyethyl cellulose, hydroxymethyl cellulose, hydroxymethyl cellulose phathalate, hydroxypropyl methylcellulose acetate succinate, methacrylate copolymer, methacrylate-ethyl acrylate copolymer, methacrylate-methyl methacrylate copolymer, carboxymethylethylcellulose, cellulose acetate phthalate, ethyl acrylate-methyl methacrylate-ethyl acrylate copolymer, ethylcellulose, and mixtures thereof.

18. The pharmaceutical composition of claim 13, wherein said coating is selected from the group consisting of hydroxylpropyl methylcellulose, hydroxypropyl cellulose, methylcellulose, hydroxyethyl cellulose, hydroxymethyl cellulose, hydroxymethyl cellulose phathalate, hydroxypropyl methylcellulose acetate succinate, methacrylate copolymer, methacrylate-ethyl acrylate copolymer, methacrylate-methyl methacrylate copolymer, carboxymethylethylcellulose, cellulose acetate phthalate, ethyl acrylate-methyl methacrylate-ethyl acrylate copolymer, ethylcellulose, and mixtures thereof.

19. The pharmaceutical composition of claim 14, wherein said coating is selected from the group consisting of hydroxypropyl methylcellulose, hydroxypropyl cellulose, methylcellulose, hydroxyethyl cellulose, hydroxymethyl cellulose, hydroxymethyl cellulose phathalate, hydroxypropyl methylcellulose acetate succinate, methacrylate copolymer, methacrylate-ethyl acrylate copolymer, methacrylate-methyl methacrylate copolymer, carboxymethylethylcellulose, cellulose acetate phthalate, ethyl acrylate-methyl methacrylate-ethyl acrylate copolymer, ethylcellulose, and mixtures thereof.

20. The pharmaceutical composition of claim 15, wherein said coating is selected from the group consisting of hydroxypropyl methylcellulose, hydroxypropyl cellulose, methylcellulose, hydroxyethyl cellulose, hydroxymethyl cellulose, hydroxymethyl cellulose phthalate, hydroxypropyl methylcellulose acetate succinate, methacrylate copolymer, methacrylate-ethyl acrylate copolymer, methacrylate-methyl methacrylate copolymer, carboxymethylethylcellulose, cellulose acetate phthalate, ethyl acrylate-methyl methacrylate-ethyl acrylate copolymer, ethylcellulose, and mixtures thereof.

\* \* \* \* \*